(12) United States Patent  
Kumar et al.

(10) Patent No.: US 8,641,417 B2  
(45) Date of Patent: Feb. 4, 2014

(54) SEALING SYSTEM FOR MEDICAL/DENTAL HANDPIECES

(75) Inventors: Ajay Kumar, Palmdale, CA (US); Kevin J. Stanton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 439 days.

(21) Appl. No.: 12/606,843

(22) Filed: Oct. 27, 2009

(65) Prior Publication Data

US 2010/0102517 A1    Apr. 29, 2010

Related U.S. Application Data

(60) Provisional application No. 61/109,430, filed on Oct. 29, 2008.

(51) Int. Cl.
*A61C 1/08* (2006.01)
*A61C 3/06* (2006.01)
*A61C 1/00* (2006.01)

(52) U.S. Cl.
USPC ............................. 433/126; 433/125; 433/131

(58) Field of Classification Search
USPC ........... 277/551, 558, 566, 567; 433/114–133
See application file for complete search history.

(56) References Cited

U.S. PATENT DOCUMENTS

| | | | | |
|---|---|---|---|---|
| 3,612,551 | A * | 10/1971 | Grabill, Jr. ................... | 277/566 |
| 3,977,084 | A * | 8/1976 | Sloan ............................ | 433/131 |
| 4,486,176 | A * | 12/1984 | Tardieu et al. ................ | 433/133 |
| 4,541,638 | A * | 9/1985 | Ogawa et al. ................. | 277/402 |
| 4,544,355 | A * | 10/1985 | Eibofner et al. ............. | 433/104 |
| 4,585,238 | A * | 4/1986 | Nicholson .................... | 277/555 |
| 4,705,038 | A * | 11/1987 | Sjostrom et al. ............. | 606/180 |
| 4,975,056 | A * | 12/1990 | Eibofner ......................... | 433/84 |
| 5,133,729 | A * | 7/1992 | Sjostrom ....................... | 606/180 |
| 5,186,472 | A * | 2/1993 | Romero et al. ............... | 277/351 |
| 5,267,860 | A * | 12/1993 | Ingram et al. ................ | 433/116 |
| 5,454,718 | A * | 10/1995 | Strohmaier ................... | 433/122 |
| 5,490,860 | A * | 2/1996 | Middle et al. ................ | 606/171 |
| 5,599,143 | A * | 2/1997 | Dusing ........................ | 408/124 |
| 6,161,838 | A * | 12/2000 | Balsells ........................ | 277/511 |
| 6,264,205 | B1 * | 7/2001 | Balsells ........................ | 277/551 |
| 6,752,629 | B2 * | 6/2004 | Suzuki et al. ................ | 433/119 |
| 7,712,745 | B2 * | 5/2010 | Clark ............................ | 277/551 |
| 7,857,322 | B2 * | 12/2010 | Fietz ............................. | 277/566 |
| 2002/0153664 | A1 * | 10/2002 | Schroeder .................... | 277/551 |
| 2005/0214712 | A1 * | 9/2005 | Shaygan ...................... | 433/125 |
| 2006/0024639 | A1 | 2/2006 | Pond | |
| 2006/0210948 | A1 * | 9/2006 | Rose et al. ................... | 433/125 |
| 2007/0273106 | A1 * | 11/2007 | Nomichi et al. ............. | 277/558 |
| 2009/0108540 | A1 * | 4/2009 | Kolb et al. ................... | 277/562 |

FOREIGN PATENT DOCUMENTS

| | | |
|---|---|---|
| EP | 1 234 551 A2 | 8/2002 |
| JP | 2003-120698 A | 4/2003 |
| WO | WO 02/07659 A2 | 1/2002 |

* cited by examiner

*Primary Examiner* — Vishal Patel
*Assistant Examiner* — Nicholas L Foster
(74) *Attorney, Agent, or Firm* — Dickstein Shapiro LLP

(57) ABSTRACT

A system for enhanced sealing against intrusion of moisture and other contaminants for medical/dental handpieces having rotating or other moving elements driven by a motor within the handpiece. The enhanced sealing includes tandem seals on stepped diameters to provide additional flow pathway impediments. The tandem seals preferably include spring seals that are positioned in opposite directions to provide enhanced sealing against pressures in two different directions that occur during the pressurization and vacuum cycles of an autoclaving process. Additional enhancements include the use of annular sealing rings with x-shaped cross sections.

5 Claims, 12 Drawing Sheets

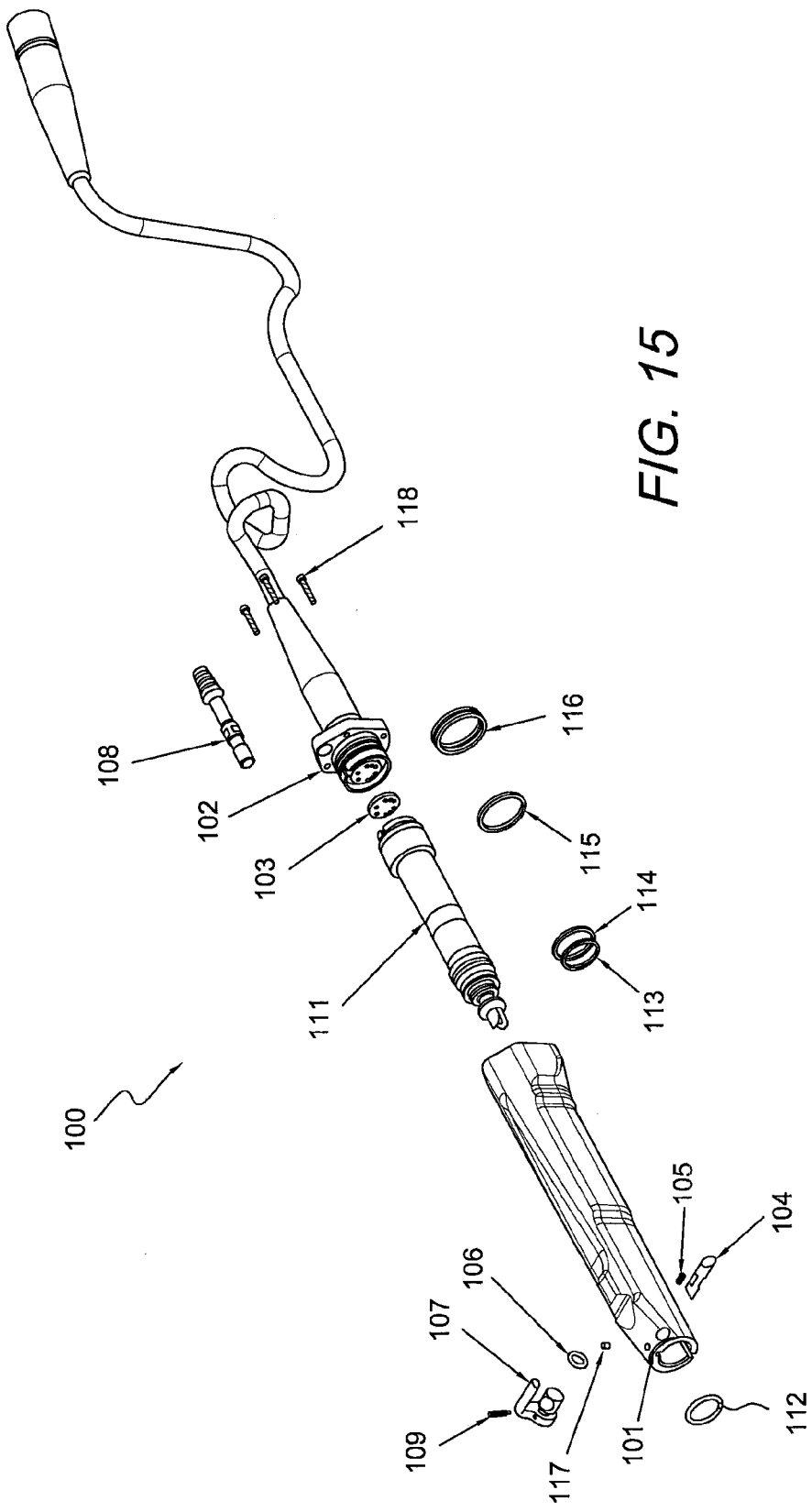

SEALING SYSTEM FOR MEDICAL/DENTAL HANDPIECES

CROSS-REFERENCE TO RELATED APPLICATIONS

This application claims the benefit of U.S. Provisional Application No. 61/109,430, filed Oct. 29, 2008, the entire disclosure of which is incorporated by reference herein.

FIELD OF THE INVENTION

The present invention relates to medical/dental handpieces having rotating or other moving elements driven by a motor within the handpiece and, in particular, to sealing systems for such medical/dental handpieces.

DESCRIPTION OF THE RELATED ART

Many DC motors fail when used in medical/dental applications as a result of migration of the moisture and saline inside the handpiece. The saline first attacks the gear box, causing the gear box to corrode. The saline then pushes the grease from the gear box into the motor, causing the rotor shaft to seize or the gears to become unlubricated. Additionally, the saline/moisture may cause the Hall-effect sensors to fail as well as shorting the electrical connections. Thereafter, depending on the insulation resistance provided by the motor, the foregoing failures create a possibility of shocking the patient, the user, or both.

BRIEF SUMMARY OF THE INVENTION

The present invention provides sealing systems for medical/dental handpieces which are sterilizable.

The sealing systems of the present invention may include step-down positioning annular seals having x-shaped cross sections (quad ring) to seal the motor housing with respect to the handpiece housing. The system may additionally include opposing tandem seals or a one piece bi-directional seal. The tandem or bi-directional seals may be spring energized lip seals such as canted coil spring seal or u-channel seals which are positioned either on step-down diameters or on the same diameter. The opposing tandem seals or bi-directional seals may be employed in combination with an excluder seal (e.g., an annular seal with an x-shaped cross section, or a U-shaped finger type spring, or unidirectional canted coil seal) to seal the output shaft against the motor housing. The excluder seal also prevents contaminants such as bio-debris from reaching the bi-directional seal and causing premature wearing of the seal.

The present invention also provides methods of minimizing the chances of saline ingression during surgery and/or steam ingression during the autoclave cycle.

BRIEF DESCRIPTION OF THE DRAWINGS

The foregoing aspects and other aspects of this disclosure are described in detail below in connection with the accompanying drawing figures in which:

FIG. 15 illustrates an exploded view of an exemplary foot-controlled shaver handpiece assembly of the present invention.

DETAILED DESCRIPTION OF THE INVENTION

Figure 1:
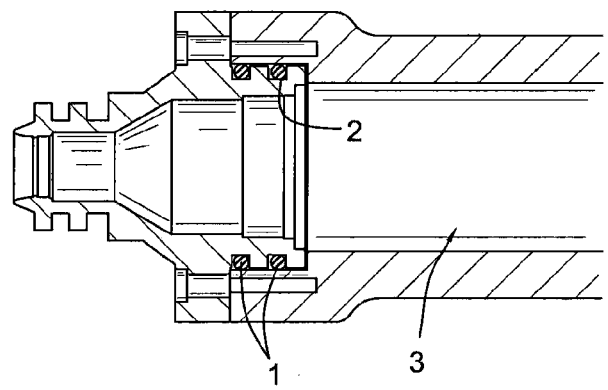
FIG. 1 illustrates a conventional O-ring sealing arrangement between components within a medical/dental handpiece.

The present invention provides sealing systems for medical/dental handpieces which are sterilizable. According to an exemplary embodiment, the sealing system includes step-down positioning annular seals having x-shaped cross sections (quad ring) to seal the motor housing with respect to the handpiece housing.

The system may additionally include opposing tandem seals or a one piece bi-directional seal. The tandem or bi-directional seals may be spring energized lip seals such as canted coil spring seal or u-channel seals which are positioned either on step-down diameters or on the same diameter. The opposing tandem seals or bi-directional seals may be employed in combination with an excluder seal (e.g., an annular seal with an x-shaped cross section, or a U-shaped finger type spring, or unidirectional canted coil seal) to seal the output shaft against the motor housing. The excluder seal also prevents contaminants such as bio-debris from reaching the bi-directional seal and causing premature wearing of the seal.

The present invention also provides a sealing system for minimizing the chances of saline ingression during surgery and/or steam ingression during the autoclave cycle.

In one embodiment, opposing tandem seals operate together to minimize steam ingression during autoclaving process and saline ingression during the surgery. The first tandem seal minimizes the probability of steam penetrating during the positive cycle (or pressurization cycle) of the autoclave and minimizes the probability of saline penetrating during surgery. The second tandem seal (closest to the motor side) operates during the vacuum cycle of the autoclave process.

In a preferred embodiment, a one piece bi-directional seal replaces the opposing tandem seals. The one piece bi-directional seal is one piece having two lip seals back to back to accomplish the same function as the opposed tandem seals. In addition to the bi-directional seal, an O-ring may be used as additional reinforcement of the seal to the output shaft. The bi-directional seal may be an OmniSpring™ 73 series spring.

Referring now to the drawings, where like elements are designated by like reference numerals, FIGS. 1-17 illustrate various embodiments of the systems of the present invention including at least one (or any combination) of the following elements: (i) step-down positioning sealing rings; (ii) opposing tandem seals or bi-directional seal; (iii) excluder seal; (iv) saline deflector; and (v) elastomeric seal provided between motor and cable.

Details of each of the elements of the systems of the present inventions are provided below:

Step-Down Positioning Sealing Rings

Figure 2:
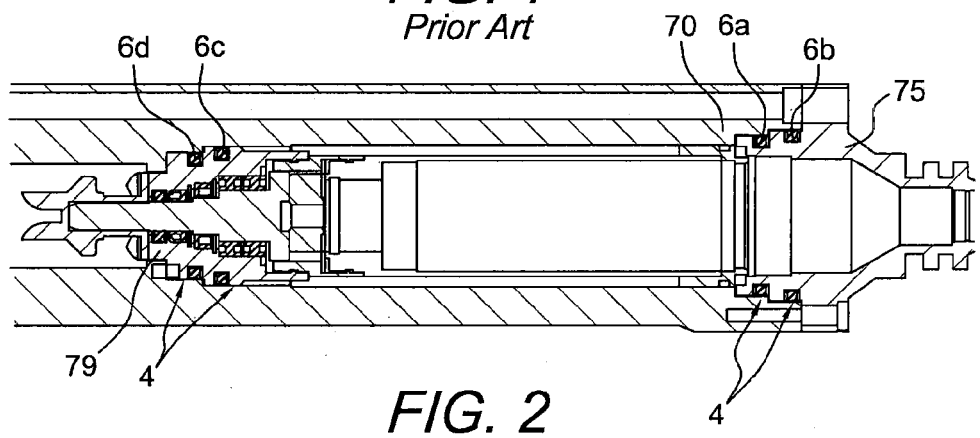
FIG. 2 illustrates an arrangement of sealing rings with different diameters to provide step-down positioning of the seals provided by the sealing rings according to an embodiment of the present invention.
Figure 2A:
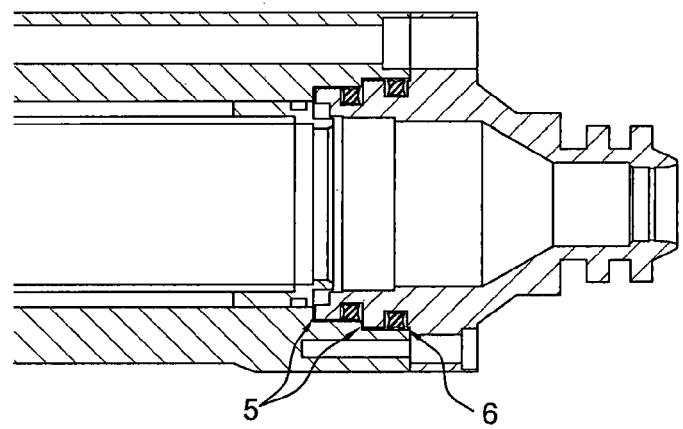
FIG. 2A illustrates a close-up view of the sealing arrangement of FIG. 2.

Referring now to FIGS. 1, 2 and 2A, FIGS. 2 and 2A illustrate an exemplary system of the present invention, with step-down positioning sealing rings in accordance with an aspect of the system and methods disclosed herein (providing improved sealing capabilities over the conventional sealing arrangement of FIG. 1).

FIG. 1 illustrates a sealing arrangement of a conventional assembly of medical/dental handpieces using two O-rings 1 that are positioned next to each other in the same diameter cavity 2. This type of O-ring arrangement allows for potential ingression of fluids into the motor cavity 3 during surgery and allows ingression of steam into the motor cavity inside the handpiece during autoclaving because the sealing arrangement only offers a single level of sealing.

To reduce the probability of fluid migration into the motor cavity, the positions of the sealing rings 6 are arranged with at least two different diameters 4 as shown in FIG. 2. As shown in the enlarged cross section in FIG. 2A, this type of sealing ring arrangement creates an interruptive flow with more flow pathway impediments (step-downs) 5 than are provided in the conventional design shown in FIG. 1. The sealing arrangement shown in FIG. 2 with seals 6a and 6b positioned within the interface between the handpiece housing 70 and the cable 75. An additional sealing arrangement is shown with seals 6c and 6d positioned within the interface between the handpiece housing 70 and the motor housing 79. The improved sealing ring arrangement can be assembled with quad-ring seals 6, which are currently available in the market and which provide better sealing surfaces than the conventional O-ring design. In particular, the quad-ring seals 6 have a generally four-lobed or x-shaped profile (or cross section) as illustrated in FIG. 2A. This cross-section arrangement provides for additional points of contact between the housing components to provide for additional sealing over the O-ring. Other annular sealing rings having non-circular cross sections may also be used.

Opposing Tandem Seals/Bi-Directional Seal

Figure 3:
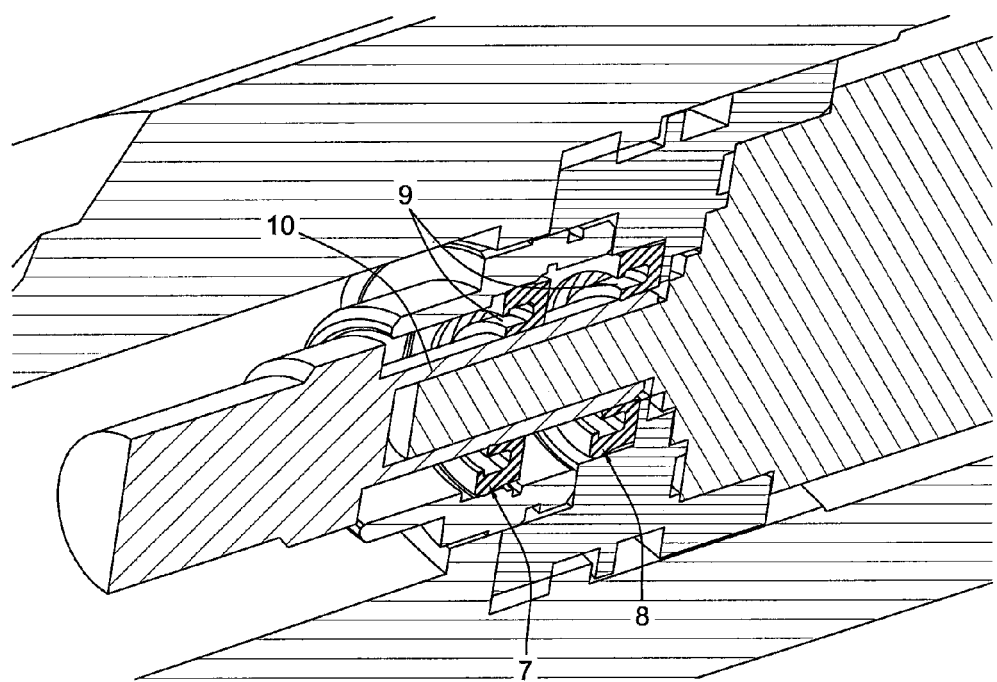
FIG. 3 illustrates a conventional motor shaft sealing arrangement using a first seal and a second seal on a single diameter shaft.
Figure 4:
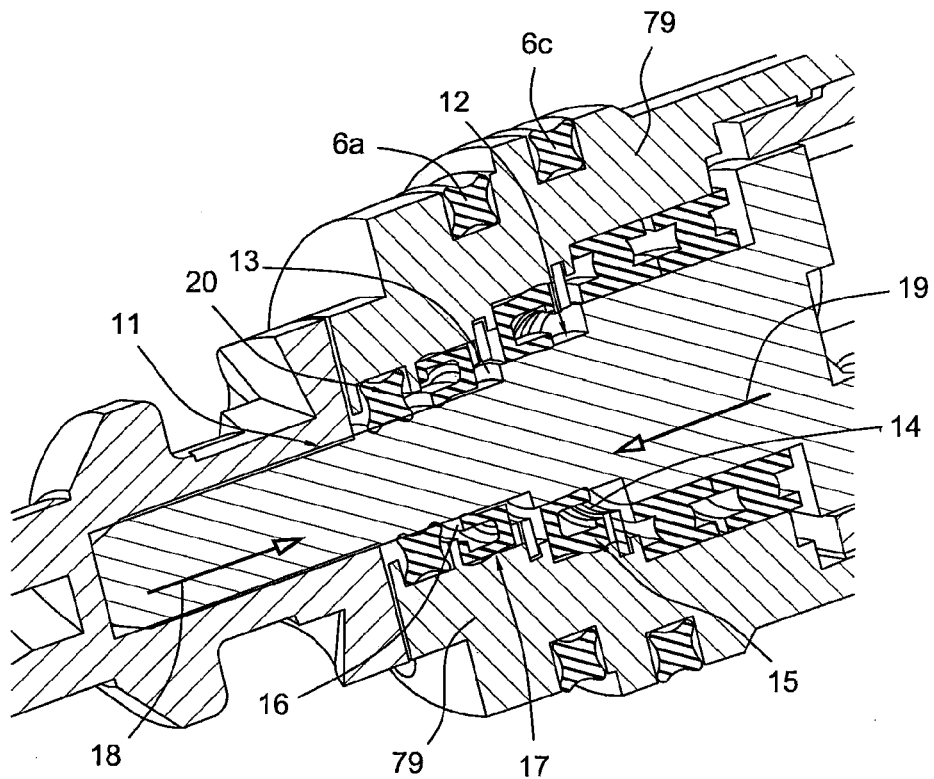
FIG. 4 illustrates an improved motor shaft sealing arrangement with tandem seals positioned on at least two different shaft diameters.
Figure 4A:
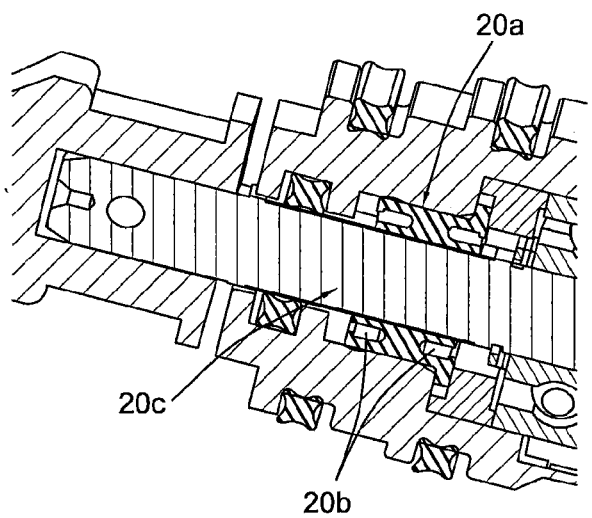
FIG. 4A illustrates a sealing arrangement having tandem seals configured as a bidirectional one piece component on a single diameter shaft.
Figure 4C:
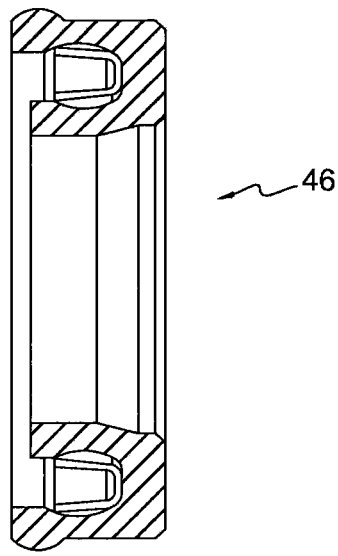
FIG. 4C illustrates the excluder seal of the sealing arrangement.

FIGS. 4 and 4A illustrate a sealing arrangement using a system of opposing tandem seals in accordance with another embodiment of the present invention (providing improved sealing capabilities over the conventional sealing arrangement of FIG. 3).

FIG. 3 illustrates a conventional motor shaft sealing arrangement with a first seal 7 towards the front or tool driver side and a second seal 8 towards the back or motor side. The two seals comprise spring seals. Each spring seal has a pair of sealing lips coupled to a common base to form a generally U-shaped or C-shaped configuration having a closed end (the base end) and an opposing open end. The sealing lips are forced apart by a spring (not shown) to cause the lips to engage the surfaces between which the lips are constrained. Pressure applied against the open end of the spring seal causes the spring seal to further expand to increase the sealing force provided by the sealing lips. In FIG. 3, the seals 7, 8 are arranged with the respective open end 9 of both seals facing towards the front (tool driver side) of the handpiece and with both seals positioned on a single diameter shaft 10. This conventional type of arrangement allows for potential ingression of fluids into the front of the motor during surgery. The arrangement also allows for potential ingression of steam during autoclaving because neither seal increases its respective sealing pressure in response to force applied in a direction away from the respective open ends, such as, during a vacuum cycle of the autoclave process. Also, in this conventional configuration, the spring seals are not protected from bio-debris such as bone chips and the like during surgery because the spring seals are the first barrier.

FIG. 4 illustrates an improved motor shaft sealing arrangement that comprises tandem spring seals 15 and 17 that are positioned on two different shaft diameters 11 and 12 to create an interruptive flow. In particular, the first seal 17 is positioned on the smaller diameter shaft 11, and the second seal 15 is positioned on the larger diameter shaft 12. The sealing arrangement of FIG. 4 includes more pathway impediments 13 than the conventional design of FIG. 3.

The seals 15, 17 are positioned on the respective shaft diameters 12 and 11 with the respective open ends 14 and 16 facing in opposite directions. In particular, the open end 14 of the second seal 15 is facing in an opposing direction from open end 16 of the first seal 17, so that the additional sealing force caused by applied pressure is activated in response to two different directional forces during an autoclaving process. One directional force, indicated by arrow 18, occurs during the pressurization (positive) cycle of the autoclaving process. The force in the direction of the arrow 18 is applied against the open end of the first seal 17 and causes the first seal to expand to increase the sealing force between the shaft 11 and the motor housing 79. The other directional force, indicated by arrow 19, occurs during the vacuum cycle of the autoclaving procedure. The force in the direction of the arrow 19 is applied against the open end of the second seal 15 and causes the second seal 15 to expand to increase the sealing force between the shaft 12 and the motor housing 79. Positioning the tandem seals in two different directions as shown in FIG. 4 ensures adequate sealing during the autoclaving process, which protects the motor.

An additional sealing component, referred to as excluder seal 20, may include an O-ring, spring seal or quad ring as shown in FIG. 4. The excluder seal 20 is advantageously positioned in front of the first seal 17 to provide additional sealing during surgery to prevent the migration of saline or other contaminants such as bio-debris into the tandem sealing region.

Figure 4B:
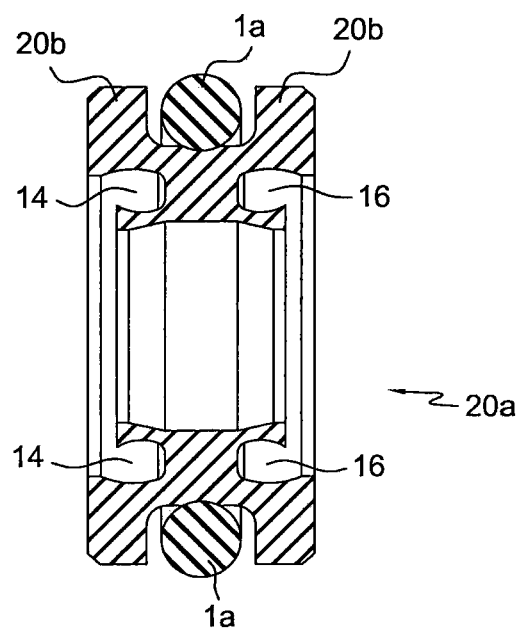
FIG. 4B illustrates the bidirectional one piece sealing component of FIG. 4A with an O-ring.

FIG. 4A illustrates an embodiment of an assembly incorporating a one-piece tandem sealing arrangement, referred to as a bi-directional seal, 20a having two opposing seals 20b facing in opposite directions. The bi-directional seal 20a is illustrated in FIG. 4B in conjunction with an O-ring 1a which provides for additional compression of the seal. The bi-directional seal is essentially two spring energized rotary lip seals mounted back-to-back in one package. The O-ring 1a is used to keep pressure on the sealing surface of the bi-directional seal as the material wears. The one-piece bi-directional seal 20a can be positioned on a single diameter shaft 20c or can positioned on a stepped down shaft as previously shown in FIG. 4.

Saline Deflector

Figure 5:
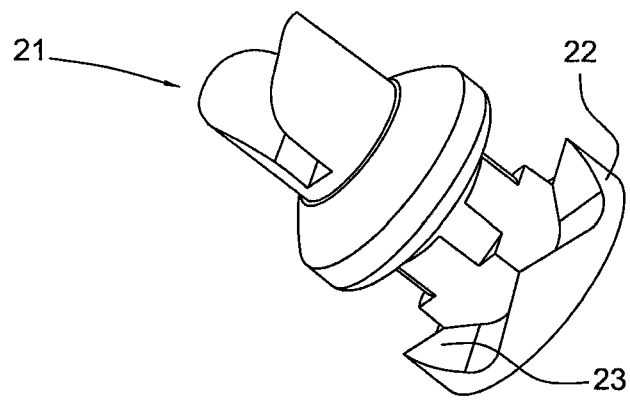
FIG. 5 illustrates a tool driver with saline deflecting features.
Figure 6:
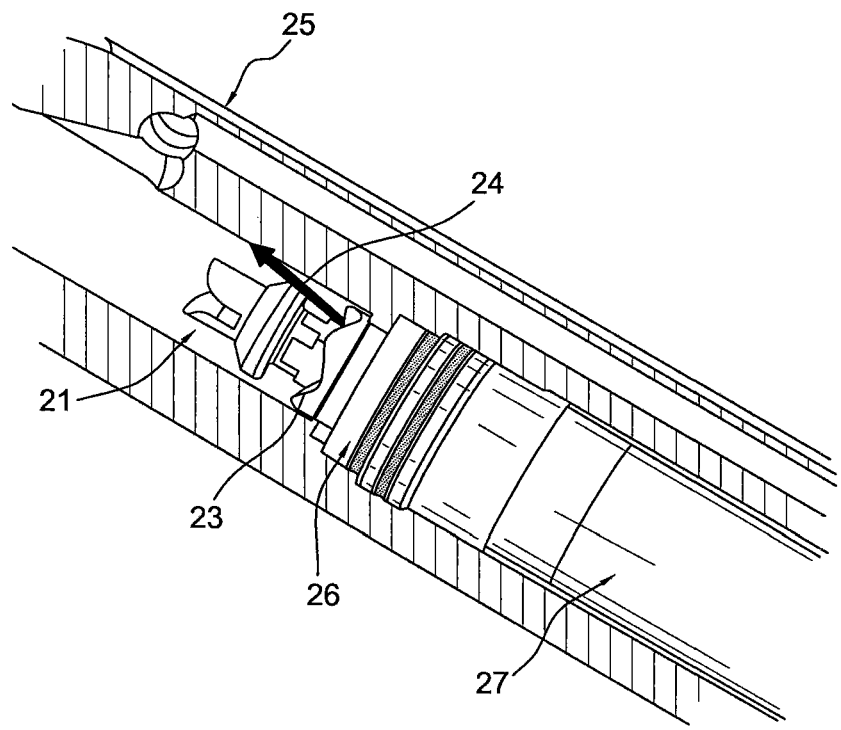
FIG. 6 illustrates the tool driver of FIG. 5 with saline deflecting features assembled in the handpiece.

FIGS. 5 and 6 illustrate a saline deflector in accordance with another embodiment of the systems and methods disclosed herein.

FIG. 5 illustrates a tool driver 21 that includes saline deflecting features 22 that prevent saline and other contaminants from entering the sealing system in front of the motor. As shown in FIG. 6, when the tool driver 21 rotates and/or oscillates, surfaces 23 on the deflecting features 22 direct fluids and or debris in a direction 24 towards the front of the handpiece 25 and away from the sealing system 26 and motor 27.

Gear System Comprising Polymer Material

Figure 7:
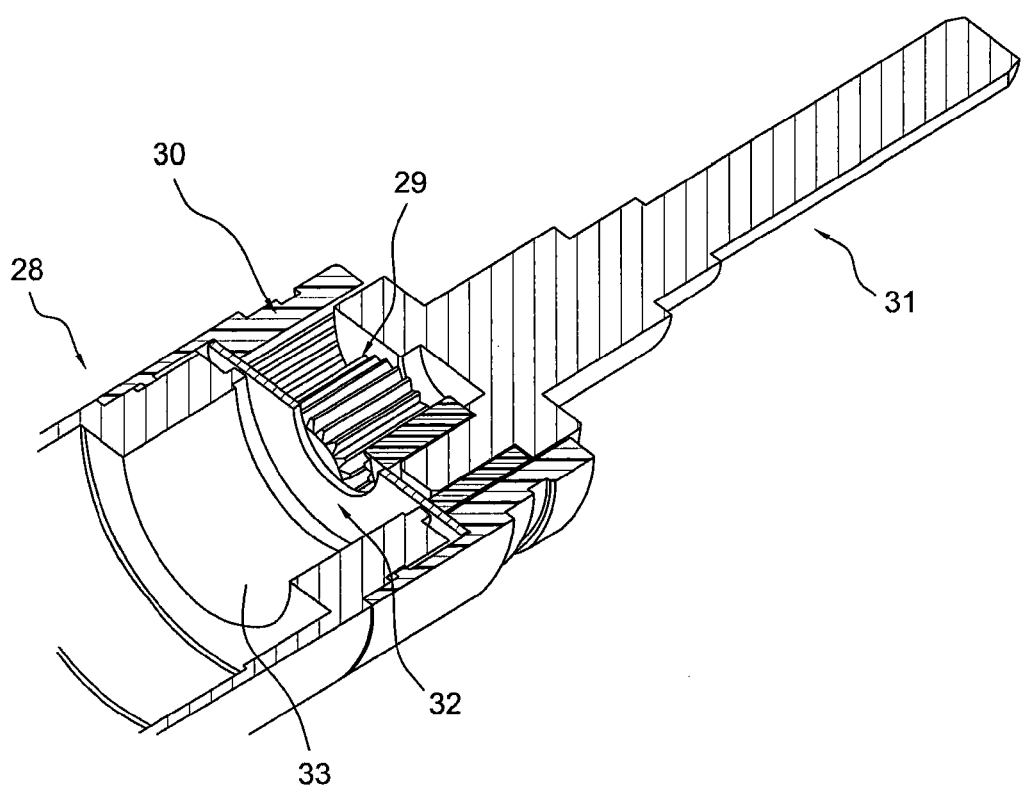
FIG. 7 illustrates a gear box with gears, and a gear box shaft assembly.

FIG. 7 illustrates an embodiment of a system that utilizes polymer gears in accordance with another embodiment of the systems and methods disclosed herein. In particular, FIG. 7 illustrates a motor 28 that utilizes gears 29 and ring gears 30 to rotate a metal shaft 31.

In conventional systems, the gears, ring gears and motor shaft comprise metal. These metal components can transmit electricity through the shaft and to the tool (not shown) that is contacting the patient, once saline has breached the seals. To avoid this condition, the gears 29 and the ring gears 30 in the embodiment of FIG. 7 comprise a liquid crystal polymer, such as, polyetheretherketone (PEEK), to provide a break in any electrical circuit that might be present from the motor shaft 31 to the output shaft. A washer 32 is advantageously placed behind the ring gear 30 to prevent the movement of air and thereby minimize the migration of grease from the gears 29 and into the motor chamber 33, thereby preserving the operational lifetime of the motor rotor shaft.

Potting Comprising Fused Glass Silica

Figure 8:
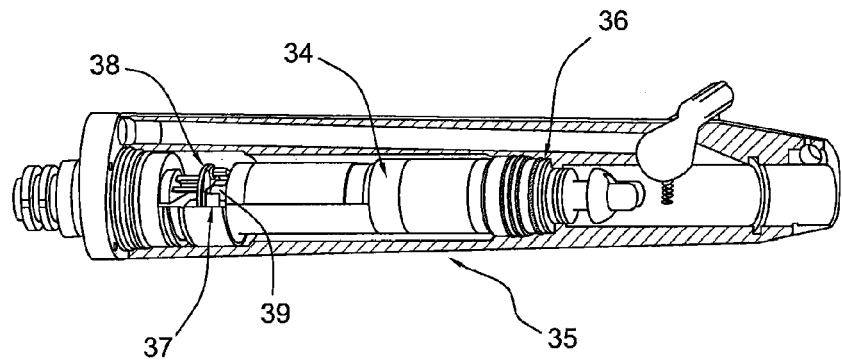
FIG. 8 illustrates a housing assembled with a motor.
Figure 9:
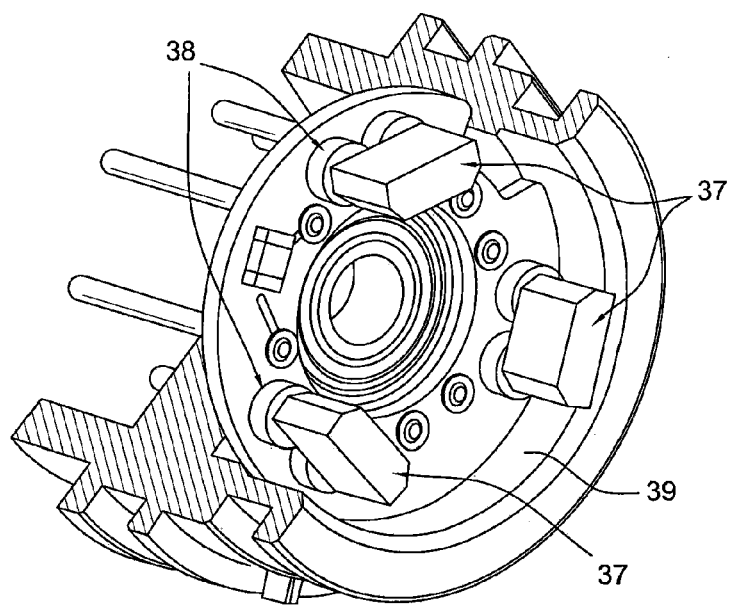
FIG. 9 illustrates the front side of the rear portion of the motor components.
Figure 10:
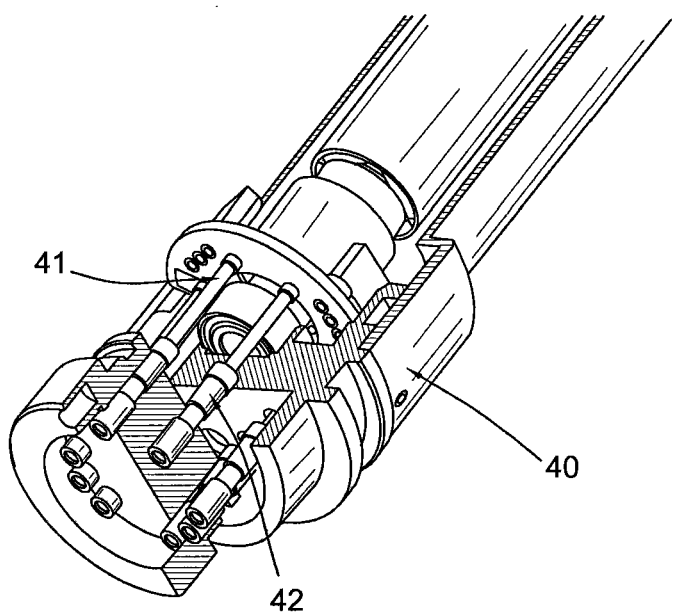
FIG. 10 illustrates the back side of the rear portion of the motor components.
Figure 11:
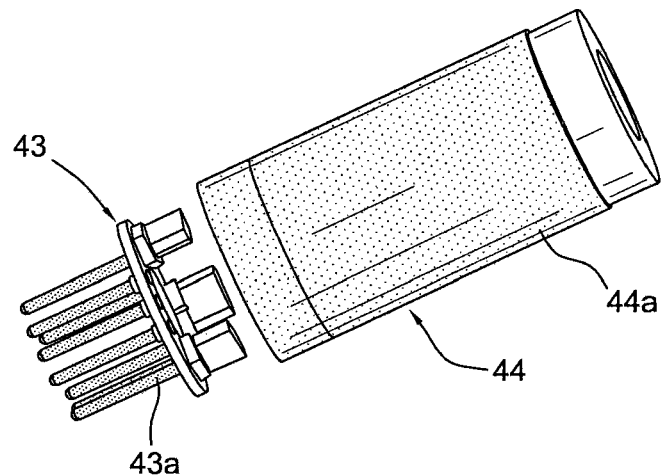
FIG. 11 illustrates the rear portion of the motor components.

FIGS. 8, 9 and 10 illustrate the effects of saline solutions on motor components, while FIG. 11 illustrates the improvements provided by fused glass silica encapsulation in accordance with another aspect of embodiments of the systems and methods disclosed herein.

The surfaces of the motor components in the market are not typically embedded in an encapsulated potting. Thus, the bare surfaces are exposed to the saline solutions that migrate into the housing and then migrate into the motor cavity as the sealing systems fail. For example, FIG. 8 shows the components of a motor 34 within a housing 35, which are exposed to saline solution that could migrate inside the motor if a sealing system 36 fails. The motor 34 has a plurality of Hall-effect sensors 37 and solder joints 38 that are exposed to the motor cavity 39. FIG. 9 shows the front side of the three Hall sensors 37 and the solder joints 38 that are exposed in the motor cavity 39. In addition, as shown in FIG. 10 for the rear portion 40 of the motor 34, when the saline migrates further, connector pins 41 can also be attacked by saline solution, which causes the connector pins to corrode, which may cause the motor to fail.

Some motor components on the market are embedded in epoxy, but epoxy materials can fail after several autoclaving cycles due to thermal expansions and contractions that cause material cracking.

As shown in FIG. 11, the system disclosed according to another embodiment of the present invention offers a complete hermetic seal of the motor cavity by encapsulating the rear motor components 43 and the front motor components 44 in a coating of fused glass silica 43a, 44a (or a similar material) that is capable of withstanding the autoclaving environment.

Excluder Seal

Figure 12:
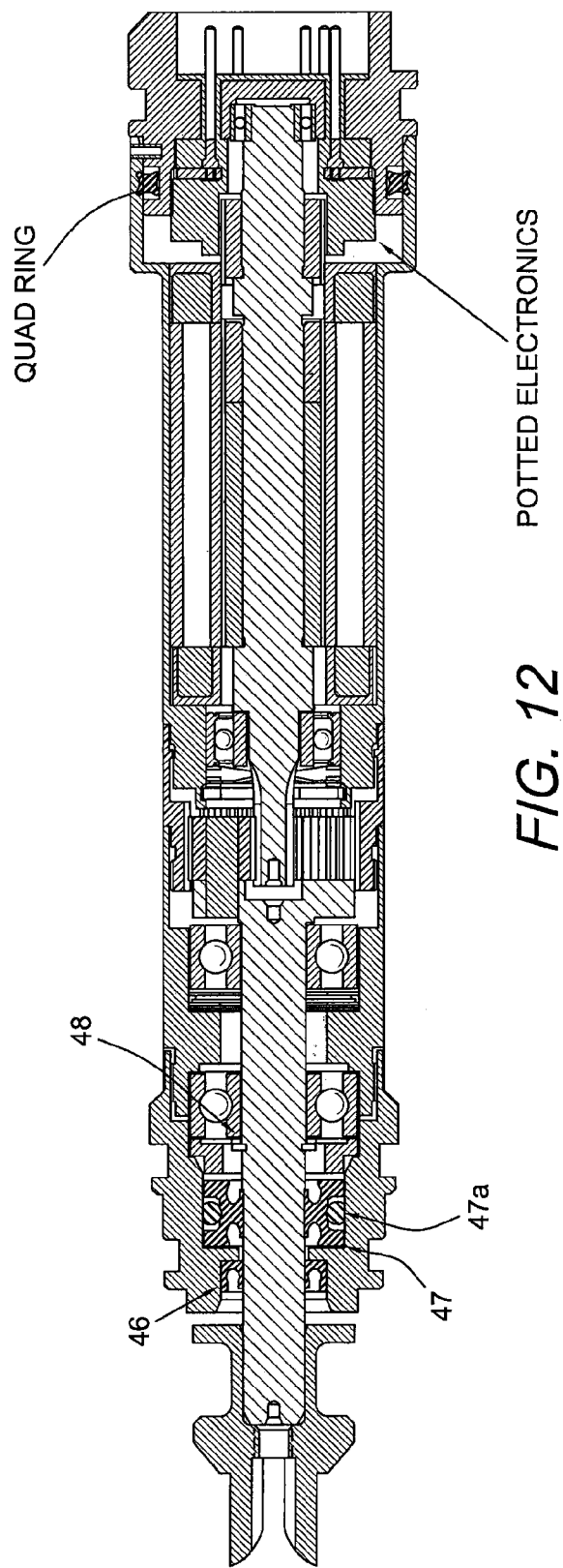
FIG. 12 illustrates a motor shaft sealing arrangement having an excluder seal and bidirectional seal with an O-ring.

FIG. 12 illustrates an improved motor shaft sealing arrangement of the present invention that comprises an excluder seal 46 and a bi-directional seal 47 with an O-ring 47a. The excluder seal 46 may be an annular seal with an x-shaped cross section, a U-shaped finger type spring, or unidirectional canted coil seal. The excluder seal may be an OmniSpring™ 22 series spring. The seal rides on a shaft 48 (for example, a solid one-piece shaft 48).

Elastomeric Interfacial Seal Between Motor and Cable

Figure 13:
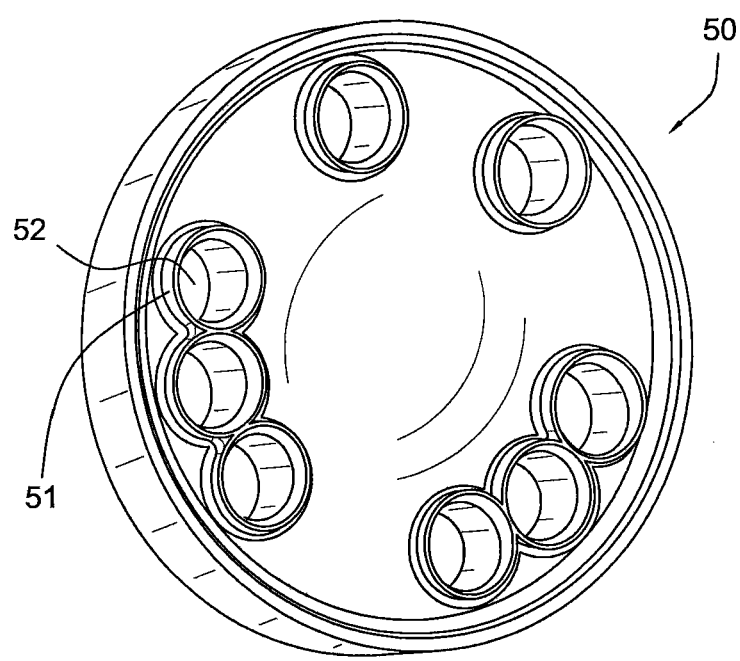
FIG. 13 illustrates an interfacial seal to be provided between the motor and the cable.
Figure 14:
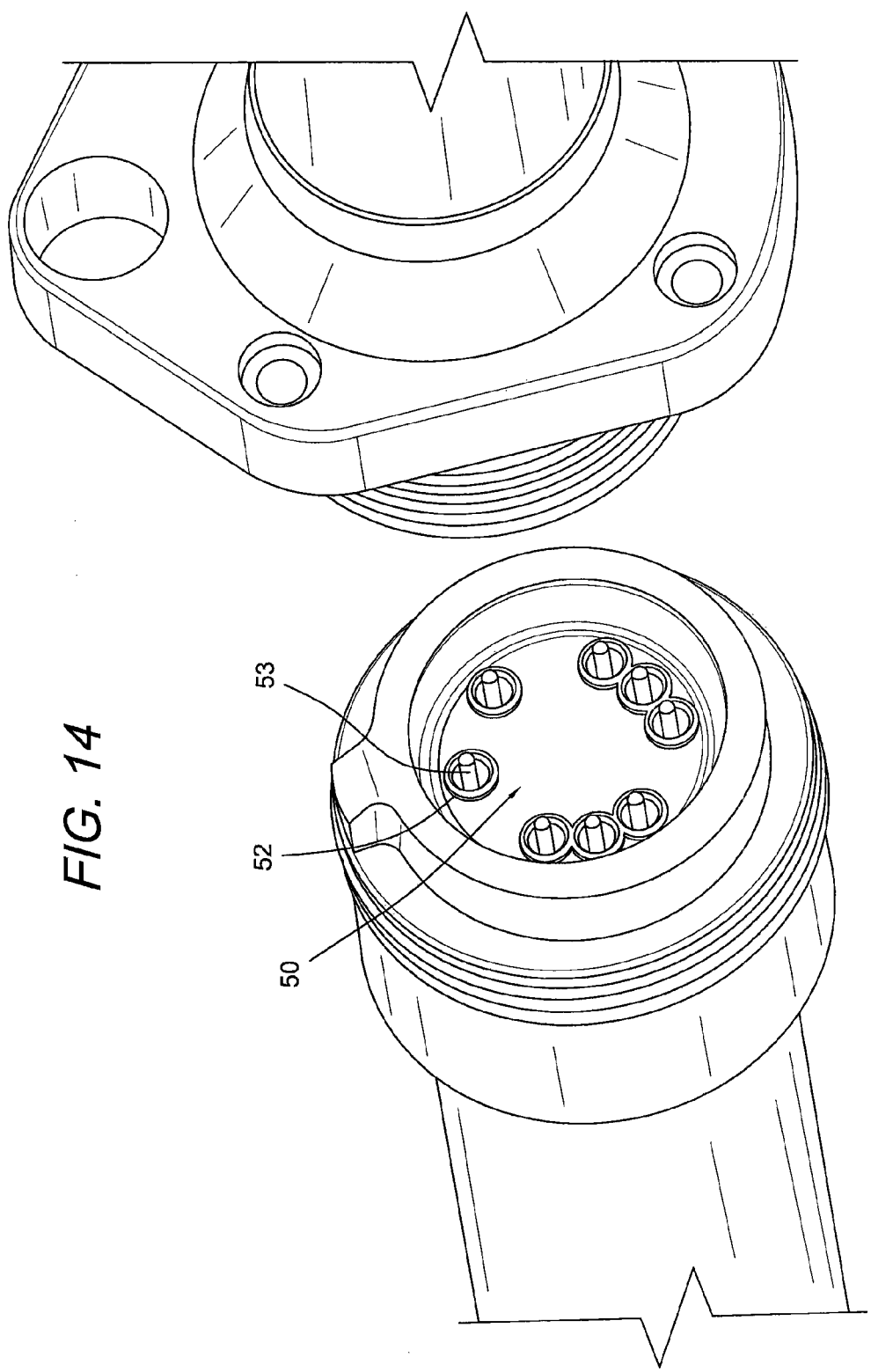
FIG. 14 illustrates the interfacial seal of FIG. 13 adjacent the motor and the cable.

FIGS. 13 and 14 illustrate an exemplary interfacial seal 50 which provides additional sealing around electrical connection of the motor to the cable or to the cable conductors. Seal 50 is composed of an elastomer and is provided with raised edges 51. As shown in FIG. 14, raised edges 51 of the elastomeric interfacial seal 50 are provided around the pin holes 52 (surrounding pins 53) which compress to make a tight seal to prevent moisture from contacting the pins 53.

Exploded Assembly Drawing

FIG. 15 illustrates an exploded view of an exemplary handpiece assembly 100 (for example, a foot-controlled shaver handpiece assembly 100) constructed in accordance with the present invention. Handpiece assembly 100 also comprises cable 102 with interfacial seal 103 (which may be similar to the elastomeric seal 50 of FIGS. 14 and 14A) disposed between cable 102 and motor shaft 111. A locking pin body 104, a spring 105, an O-ring 106, a suction fitting 108, and a set of screws 109 secure suction valve 107 to housing 101.

As also shown in FIG. 15, handpiece assembly 100 also includes motor shaft 111 which is secured to housing 101 and sealed by O-ring 112, and a series of Quad rings 113, 114, 115. Quad ring 116 seals cable 102 to shaft 111. FIG. 16 also illustrates screw 117 for locking pin 104 and screw 118 for an endcap attached to cable 102. Motor shaft 111 of the assembly 100 may be provided with step-down positioning sealing rings and/or with opposing tandem seals such as the step-down positioning sealing rings 6 of FIG. 2A or tandem seals 15, 17 of FIG. 4. The gear system of the shaft 111 may be also formed of a polymer material (such as PEEK, for example), similar to gear 29 of FIG. 7.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A system for sealing a rotating shaft of a motor in a handpiece subject to pressure applied in a first direction during a pressurization cycle of an autoclaving process and subject to pressure applied in a second opposite direction during a vacuum cycle of the autoclaving process, comprising:

a rotating shaft coupled to a tool during a medical/dental procedure;

a first spring seal positioned at a first location on the rotating shaft, the first spring seal being fixed to a housing of the motor, the first spring seal having a base at a closed end and a pair of sealing lips attached to the base at the closed end, the sealing lips being spaced apart at an open end, the open end of the first spring seal being directed toward a force applied during the pressurization cycle to cause the first spring seal to expand during the pressurization cycle of the autoclaving process to increase a sealing force provided by the first spring seal during the pressurization cycle a second spring seal positioned at a second location on the rotating shaft, the second spring seal being fixed to the housing of the motor, the second spring seal having a base at a closed end and a pair of sealing lips attached to the base at the closed end, the sealing lips being spaced apart at an open end, the open end of the second spring seal being directed toward a force applied during the vacuum cycle to cause the second spring seal to expand during the vacuum cycle of the autoclaving process to increase a sealing force provided by the second spring seal during the vacuum cycle, wherein the sealing lips of the open end of the first spring seal face in an opposing direction from the sealing lips of the open end of the second spring seal, wherein the first spring seal is spaced apart from the second spring seal;

an excluder seal mounted on the shaft to block particles produced by the tool from reaching the first spring seal; and an interfacial seal disposed between the rotating shaft of the motor and an electrical connection of the motor to a cable or cable conductors.

2. The system of claim 1, wherein the excluder seal comprises a u-channel finger spring.

3. The system of claim 1, wherein the rotating shaft is coupled to an electrically powered motor by a plurality of gears, and wherein the gears comprise a polymer.

4. The system of claim 3, wherein the polymer comprises polyetheretherketone (PEEK).

5. A system for sealing the interface between an inner housing and an outer housing of a medical/dental handpiece including a motor shaft, the system comprising:

a cavity in the outer housing, the cavity having a first interface section having a first inner diameter, the cavity having a second interface section having a second inner diameter, the first inner diameter smaller than the second inner diameter;

an inner housing having a third interface section having a first outer diameter, the third interface section fitting in the first interface section of the cavity, the inner housing having a fourth interface section having a second outer diameter, the fourth interface section fitting in the second interface section of the cavity;

a first annular seal positioned between the first interface section of the cavity and the third interface section of the inner housing, the first annular seal having an x-shaped cross section;

a second annular seal positioned between the second interface section of the cavity and the fourth interface section of the inner housing, the second annular seal having an x-shaped cross section, wherein the first annular seal is spaced apart from the second annular seal;

an excluder seal mounted on the motor shaft to block particles produced by the medical/dental handpiece to reach the first annular seal; and an interfacial seal disposed between the motor shaft and an electrical connection of the motor shaft to a cable or cable conductors.

* * * * *